United States Patent
Zhang et al.

[11] Patent Number: 6,117,293
[45] Date of Patent: Sep. 12, 2000

[54] METHOD FOR PRODUCING HYDROPHILIC MONOMERS AND USES THEREOF

[75] Inventors: Tianhong Zhang, Rockport; Noriko Kusukawa, Camdem, both of Me.

[73] Assignee: BioWhittaker Molecular Applications, Inc., East Rutherford, N.J.

[21] Appl. No.: 09/127,770

[22] Filed: Jul. 31, 1998

[51] Int. Cl.[7] ................................................. G01N 27/26
[52] U.S. Cl. ......................... 204/455; 204/469; 525/509
[58] Field of Search ................................. 204/456, 465, 204/469, 470, 455, 451; 427/2.11, 2.1; 525/509, 540, 926, 927

[56] References Cited

U.S. PATENT DOCUMENTS

| | | | |
|---|---|---|---|
| 2,593,888 | 4/1952 | Jones | 564/143 |
| 4,101,461 | 7/1978 | Strop et al. | 521/32 |
| 5,055,517 | 10/1991 | Shorr et al. | 524/813 |
| 5,202,007 | 4/1993 | Kozulic et al. | |
| 5,319,046 | 6/1994 | Kozulic et al. | |
| 5,552,028 | 9/1996 | Madabhushi et al. | |
| 5,567,292 | 10/1996 | Madabhushi et al. | |
| 5,863,551 | 1/1999 | Woerly | 424/423 |

FOREIGN PATENT DOCUMENTS

| | | |
|---|---|---|
| 60-262805 | 12/1985 | Japan . |
| 61-068454 | 4/1986 | Japan . |
| 93/11174 | 6/1993 | WIPO . |
| 97/16462 | 5/1997 | WIPO . |

OTHER PUBLICATIONS

Chen, F. (1986). "N–(Hydroxyalkyl)acrylamide Copolymers for Corrosion Control." ACS Symposium Series 322:282–290, Month Unknown.

Chiari, M. et al. (1995). "New types of separation matrices for electrophoresis." *Electrophoresis* 16:1815–1829, Month Unknown.

Saito, N et al. (1996). "Synthesis and Hydrophilicity of Multifunctionally Hydroxylated Poly(acrylamides)." *Macromolecules* 29:313–319, Month Unknown.

Simo–Alfonso, E. et al. (1996). "Novel acrylamido monomers with higher hydrophilicity and improved hydrolytic stability: I. Synthetic route and product characterizationn." *Electrophoresis* 17:723–731, Month Unknown.

Simo–Alfonso, E. et al. (1996). "Novel acrylamido monomers with higher hydrophilicity and improved hydrolytic stability: II. Properties of N–acrylolaminopropanol." *Electrophoresis* 17:732–737, Month Unknown.

PCT International Search Report dated Nov. 19, 1999, 3 pages.

*Primary Examiner*—Jill Warden
*Assistant Examiner*—Alex Noguerola
*Attorney, Agent, or Firm*—Woodcock Washburn Kurtz Mackiewicz & Norris LLP

[57] ABSTRACT

The invention relates to a method for producing hydrophilic monomers which are particularly useful for electrophoresis and to electrophoresis compositions and coating compositions. The method uses the steps of reacting a (meth)acryloyl with an aminoalcohol in the presence of a base in a polar solvent, optionally filtering an aqueous solution of the reaction product, deionizing an aqueous solution of the reaction product, and removing the solvent.

17 Claims, 2 Drawing Sheets

METHOD FOR PRODUCING HYDROPHILIC MONOMERS AND USES THEREOF

TECHNICAL FIELD

This invention relates to a method for producing hydrophilic monomers, which are particularly useful for electrophoresis, and to electrophoresis compositions, more particularly, to an electrophoresis gel composition that is hydrolytically stable and has high resolution for biological macromolecule separations. The invention also relates to the preparation of electrophoresis compositions, electrophoresis gels, and coating compositions. The invention further relates to the use of said compositions and gels for high resolution electrophoretic separations of proteins, nucleic acids, and other biological macromolecules.

BACKGROUND ART

The publications and other materials used herein to illuminate the background of the invention, and in particular, cases to provide additional details respecting the practice, are incorporated herein by reference.

Electrophoresis gels have been widely used for the separations of biological macromolecules such as proteins, nucleic acids, and the like. There are essentially two types of gels in use: agarose gels and polyacrylamide gels. Polyacrylamide gels, in general, have higher resolving power than agarose gels. Since gel casting is rather tedious and the quality of handcast gels is inconsistent, there is a need for precast, "ready to use" gels. Generally, precast gels are manufactured and supplied in buffers of pH between 8 and 9. Under these conditions, precast agarose gels are stable, and have a shelf life of one year at 4° C. However, precast polyacrylamide gels are unstable, and depending on use, have a shelf life of only three months at 4° C. As precast polyacrylamide gels age in alkaline conditions (pH above 7), the electrophoretic mobility of biological macromolecules through these gels decreases and the separation resolution deteriorates. The short shelf life of precast polyacrylamide gels is primarily attributed to the hydrolytic degradation of acrylamide moieties in the gel, while the crosslinking units, usually N,N'-methylene bisacrylamide, are relatively stable. Due to the short shelf life of precast polyacrylamide gels, it is difficult for a manufacturer to mass produce and to store large quantities of gels, and it is inevitable that some customers have to throw away some unused but "expired" gels. Therefore, it is highly desirable to have a gel that has a similar resolution to polyacrylamide gel, but a longer shelf life. Since the manufacturing and application of precast polyacrylamide gels are well established, it is even more desirable to have a stable, high resolution gel system that can be manufactured and used in the same manner as polyacrylamide gels.

Recognizing the fact that the short shelf life of precast polyacrylamide gels is due to the hydrolytic degradation of acrylamide moieties in alkaline condition, Takeda et al. (U.S. Pat. No. 5,464,516), Engelhorn et al. (U.S. Pat. No. 5,578,180) and Bjellqvist et al. (WO 96/16724) developed neutral buffer systems to replace the Tris.HCl buffer (pH= 8.8) in sodium dodecyl sulfate (SDS) polyacrylamide gels, and indeed improved the shelf life of precast polyacrylamide gels. However, the gel running buffer has to be changed accordingly, and the protein separation patterns that are obtained from these systems are different from traditional SDS polyacrylamide electrophoresis based on the Laemmli system (Laemmli, *Nature* 277:680–685 (1970)).

Several vinyl-based monomers were proposed to replace acrylamide in the standard polyacrylamide gel system in order to improve gel stability. Shorr and Jain (U.S. Pat. No. 5,055,517) disclosed the use of N-mono- or di-substituted acrylamide monomers, such as N,N'-dimethylacrylamide (DMA), in electrophoresis gels. Although DMA is more stable than acrylamide, DMA is very hydrophobic and is useful in only a limited number of electrophoretic applications, such as for certain types of nucleic acid analyses.

Kozulic and Mosbach (U.S. Pat. No. 5,319,046) disclosed the use of N-acryloyl-tris-(hydroxymethyl)aminomethane (NAT), and Kozulic (U.S. Pat. No. 5,202,007) disclosed the use of sugar-based acrylamide derivatives in electrophoresis gels. Because of the presence of several hydroxyl groups in the monomers, these monomers are extremely hydrophilic. However, Chiari et al (*Electrophoresis* 15:177–186 (1994)) reported that NAT is less stable than acrylamide. On the basis of molecular modeling, Miertus et al (*Electrophoresis* 15:1104–1111 (1994)) concluded that, when there are two atoms between the amide linkage and the hydroxyl group (as is the case for NAT, sugar-based acrylamide derivatives, and N-(2-hydroxyethyl)acrylamide), the hydroxyl group facilitates the hydrolysis of amide linkages.

In a series of articles and patent application, Righetti et al. (WO 93/11174; *Electrophoresis* 15:177–186 (1994); *Electrophoresis* 16:1815–1829 (1995)) disclosed the use of N-mono- and di-substituted hydroxyethoxyethyl-(meth) acrylamides and their analogs in electrophoresis gels. The formula of the monomers disclosed by Righetti et al. in these references is:

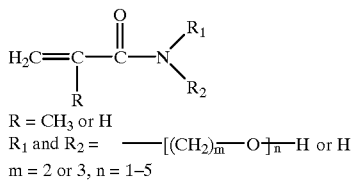

R = CH₃ or H
R₁ and R₂ = ──[(CH₂)ₘ─O─]ₙ─H or H
m = 2 or 3, n = 1–5

N-(Hydroxyethoxyethyl)acrylamide (HEEAA) was identified as the preferred monomer, because of its extreme hydrophilicity and resistance to alkaline hydrolysis.

However, Righetti et al. (WO 97/16462; *Electrophoresis* 17:723–731 (1996); *Electrophoresis* 17:732–737 (1996); *Electrophoresis* 17:738–743 (1996)) subsequently reported that the HEEAA monomer had a peculiar tendency to auto-polymerize during storage as a 50% aqueous solution at 4° C., even in the presence of free radical inhibitor. In view of this auto-polymerization tendency of HEEAA, Righetti et al. disclosed in these references the use of N- mono- and di-substituted hydroxyalkyl-(meth)acrylamides as an alternative in electrophoresis gels. The formula of the monomers disclosed by Righetti et al. in these references is:

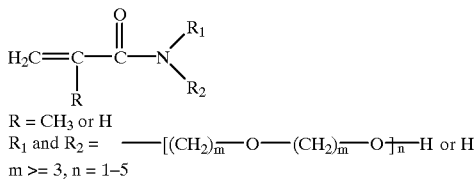

R = CH₃ or H
R₁ and R₂ = ──[(CH₂)ₘ─O──(CH₂)ₘ─O─]ₙ─H or H
m >= 3, n = 1–5

N-(Hydroxypropyl)acrylamide (HPAA) was claimed by Righetti et al. to be extremely hydrophilic and resistant to alkaline hydrolysis. However, there have been no further reports on HPAA-based gels by Righetti's group or other groups, and there have been no HPAA-based commercial products.

Although N-(2-hydroxyethyl)acrylamide (HEAA) is an analog of the N-(hydroxyalkyl) acrylamides disclosed by Righetti (WO 97/16462), it has never been reported or even mentioned as a monomer for electrophoresis gels. For example, Righetti specifically excludes HEAA in his patent applications and references. This is partially because HEAA was not commercially available, but more importantly, HEAA was believed to be unstable to hydrolysis, like N-acryloyl-tris-(hydroxymethyl)aminomethane (NAT) (*Electrophoresis* 15:1104–1111 (1994)).

Although several preparation methods for HEAA have been reported in the literature, none of them is satisfactory to provide high-purity HEAA with high yield and easy scale-up ability. Saito et al (*Macromolecules* 29:313–319 (1996)) described a two-phase method for the preparation of HEAA. The organic phase contains acryloyl chloride and ethyl acetate solvent, and the aqueous phase contains sodium hydroxide and ethanolamine. The product is recovered from the organic phase, and further purified by silica gel chromatography. There are two inherent disadvantages with this method, however. First, HEAA is readily soluble in water, and ethyl acetate extraction is not efficient. Second, it is impractical to produce large quantities of HEAA by silica gel chromatography.

Chen (ACS *Symposium Series* 322:283–290 (1986)) disclosed a one-phase method in which acryloyl chloride was reacted with two equivalents of ethanolamine in acetonitrile. Although high-yield HEAA can be obtained in acetonitrile solution, no purification method was provided, other than removing acetonitrile by distillation. Removal of acetonitrile in this manner results in some polymerization of the HEAA monomer during purification.

Righetti et al (WO 97/16462; *Electrophoresis* 17:723–731 (1996)) disclosed another onephase method for the preparation of N-(hydroxyalkyl)acrylamides. They reported that ethanol is the best solvent for this reaction. Since ethanol is reactive towards acryloyl chloride, the reaction has to be conducted between –30° C. and –70° C. Silica gel was also used for further purification.

Murashige and Fujimoto (JP 61-068454 and JP 61-000053) disclosed a method in which N-(hydroxyethyl) acrylamide was prepared by treating ethanolamine with $C_{1-22}$ alkyl acrylate or acrylic acid. The monomer was directly converted to its polymer, and no monomer purification method was disclosed.

Thus, there is a need to develop additional hydrophilic monomers for preparing electrophoresis compositions, and particularly electrophoresis gels having the combined properties of hydrolytic stability and high resolution. This need in the art is satisfied by the present invention, as described in further detail below.

There further is a need to develop a method for producing high purity N-(hydroxyethyl)acrylamide (HEAA) and similar hydrophilic monomers simply and on a large scale. This need is satisfied by the present invention, as described in further detail below.

DISCLOSURE OF THE INVENTION

It is an object of this invention to provide a method for the preparation of high-purity hydrophilic acrylamide or methacrylamide derivatives containing hydroxy groups simply and on a large scale.

It is also an object of this invention to provide compositions useful for electrophoresis, including pre-cast gels and monomer compositions for coating capillaries or for preparing electrophoresis gels or polymers, for the separation of biological macromolecules, such as proteins, nucleic acids and the like.

It is a further object of this invention to provide a gel composition for electrophoretic separations, which has combined high resolution and hydrolytic stability.

According to one aspect of the present invention, hydrophilic monomers are produced by reacting (meth)acryloyl chloride with an aminoalcohol in a polar solvent, which favors amidation in the presence of a base. The reaction mixture is subjected to deionization, solvent removal and optionally, filtration. In one embodiment of the invention, water is added to the reaction mixture, the resulting aqueous solution is deionized, and the solvent is removed from the deionized aqueous solution to produce an aqueous solution of the hydrophilic acrylamide or methacrylamide derivatives containing hydroxy groups free of solvent. In a second embodiment of the invention, water is added to the reaction mixture, the solvent is removed from the resulting aqueous solution, and the resulting aqueous solution free of solvent is deionized to produce an aqueous solution of the hydrophilic acrylamide or methacrylamide derivatives containing hydroxy groups. In a third embodiment, the reaction mixture is first filtered to remove the salt byproduct prior to the addition of water for deionization or for the solvent removal step.

According to a second aspect of the invention, compositions useful for electrophoretic applications are provided. These compositions may be used for coating capillary tubes used for capillary electrophoresis or to prepare a linear polymer as the sieving medium for capillary electrophoresis. In this embodiment, the composition comprises an aqueous solution of either the hydrophilic monomer (for coating) or the linear polymer (for use as a sieving medium). The composition may also be used to prepare formulated solutions, which can be used to prepare precast gels or to prepare gels prior to use. Such gels are useful for DNA sequencing or other macromolecule separations. In this embodiment, the composition comprises a hydrophilic N-(hydroxyalkyl)(meth)acrylamide or N,N-di (hydroxyalkyl)(meth)acrylamide monomer, an optional comonomer, a bifunctional crosslinker, such as N,N'-methylene bisacrylamide (BIS), a buffer and an optional denaturant. An initiator is added to effect the formation of the gel.

According to a third aspect of the invention, a stable, high-resolution electrophoresis gel is prepared by the free radical copolymerization of a hydrophilic monomer as described herein, preferably N-(2-hydroxyethyl)acrylamide (HEAA), an optional comonomer, and a bifunctional crosslinker, such as N,N'-methylene bisacrylamide (BIS), in a buffer solution in a plastic or glass gel mold.

DETAILED DESCRIPTION OF THE INVENTION

Figure 1:
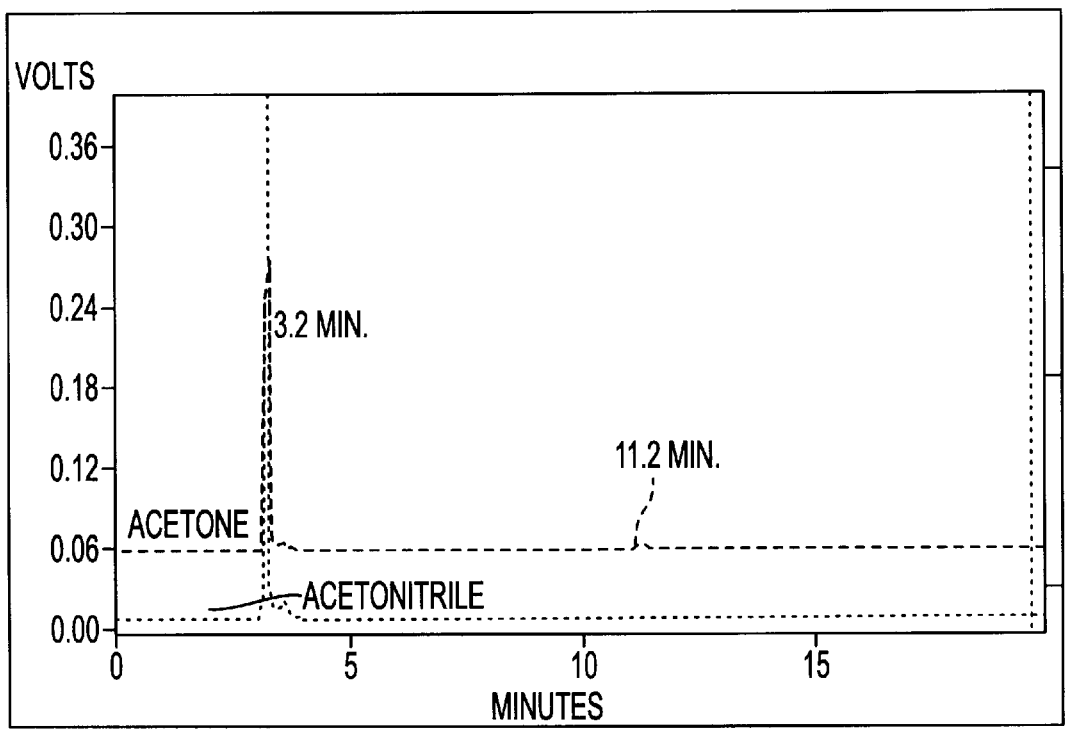
FIG. 1 shows a high performance liquid chromatography (HPLC) chromatogram of HEAA reaction products prepared in acetone (top graph line) or acetonitrile (bottom graph line). HPLC analysis was conducted with a Rainin Dynamax Model SD-200 solvent delivery system equipped with a UV detector. The following running condition was used: Column, Reverse Phase Hypersil ODS 5 mm from Aldrich; Mobile Phase, 10% acetonitrile and 90% water mixture; Flow Rate, 1.0 mL/minute; Detection, 254 nm.

The preparation of high purity hydrophilic monomers for use in electrophoresis, especially HEAA, has been a challenge for two reasons. First, HEAA is prepared by reacting acryloyl chloride with a bifunctional compound, ethanolamine. While amidation of the amine group on ethanolamine is the desired reaction, esterification of the hydroxyl group on ethanolamine is also possible. Therefore, in addition to the desired product, HEAA, there are two possible byproducts, aminoethyl-acrylate and acrylamido-ethyl-acrylate. The chemical structures of these compounds are shown below:

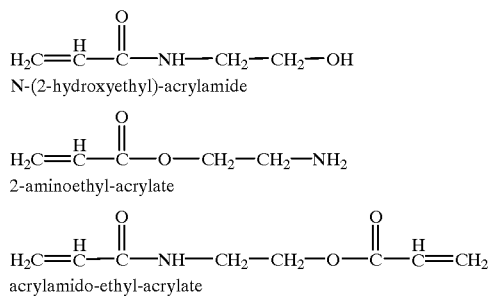

While aminoethyl-acrylate can be removed by ion-exchange, the separation of the hybrid crosslinker, acrylamido-ethyl-acrylate, from the desired monomer, HEAA, is difficult. In order to minimize or eliminate esterification, it is preferred to conduct the reaction at low temperature. Secondly, HEAA is a liquid with a high boiling point, and neither crystallization nor vacuum distillation is suitable as a purification method. For small-quantity preparation, silica gel chromatography has to be used. In addition, as a result of the present invention, it was discovered that HEAA has a high tendency to self-polymerize.

According to one aspect of the present invention, a method is provided for preparing hydrophilic monomers having high purity in a simple manner and on a large scale. The method to prepare high purity hydrophilic monomers has the following advantages over prior art methods: (1) the reaction can be conducted at temperatures about or above 0° C. without esterification; (2) self-polymerization of hydrophilic monomers, especially those which underwent self-polymerization by prior art methods, is eliminated by keeping the monomer in solution throughout the process; (3) the hydrophilic monomer is purified by deionization, preferably by ion-exchange rather than silica gel columns, as in the prior art. The method of the present invention for preparing the hydrophilic monomers involves three or four steps, as described below. The steps can be conducted in several combinations, as described below.

One step involves the reaction of a (meth)acryloyl chloride having the following formula

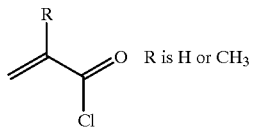 R is H or CH$_3$ with an equivalent amount of an aminoalcohol having the following formula

NH(R$_1$)(R$_2$OH)

wherein R$_1$ is H, C$_1$–C$_6$ alkyl, (C$_1$–C$_3$ alkyl-X—)$_n$—H, C$_1$–C$_3$ alkyl-C(O)—OR$_3$ or (C$_1$–C$_3$ alkyl-C(O)—NH—R$_4$, R$_2$ is C$_2$–C$_6$ alkyl, (C$_1$–C$_6$ alkyl-X—)$_n$—H, C$_1$–C$_3$ alkyl-C(O)—OR$_3$ or (C$_1$–C$_3$ alkyl-C(O)—NH—R$_4$, R$_3$ is C$_1$–C$_3$, R$_4$ is H or C$_1$–C$_3$, X is O or S, n is 1–5, each alkyl is a linear or branched chain alkyl and is unsubstituted or substituted with halogen, hydroxy or other non-ionizable group in the presence of a base in a polar solvent at a temperature below 20° C., preferably below 5° C., and most preferably below 0° C. The solvent is selected such that (1) it favors amidation and disfavors esterification. In addition, in a preferred embodiment, the solvent is further selected such that (2) it is anhydrous to avoid hydrolysis of the (meth) acryloyl chloride. In a more preferred embodiment, the solvent is further selected such that (3) it is aprotic, (4) it has a lower boiling point than water and (5) the ammonium chloride salt has a low solubility in the solvent. The selection of solvent other than for factor (1) can be chosen on the basis of the further steps described below. Any organic solvent which meets these criteria can be used. Suitable solvents include, but are not limited to, acetonitrile and ethanol The base may be the aminoalcohol or a tertiary amine. Suitable tertiary amines include, but are not limited to, triethylamine and pyridine. A preferred base is one which forms insoluble HCl salts in the organic solvent. The temperature at which the reaction is conducted is dependent on the solvent used, and is selected to avoid esterification and polymerization of the monomer as it is being prepared. For example, if the solvent is acetonitrile, a temperature below 5° C. is preferred, whereas if the solvent is ethanol, a temperature below −20° C. is preferred. It is preferred to use acetonitrile as the polar solvent. The reaction is preferably conducted at a 0.5–3.0 M concentration of reactants, more preferably at a 1.0–2.0 M concentration of reactants, and most preferably at a 2.0 M concentration of reactants. The reaction produces a hydrophilic monomer having the following formula

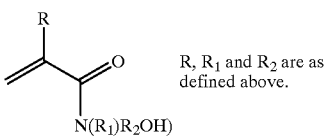 R, R$_1$ and R$_2$ are as defined above.

A second step involves the filtration of the reaction mixture to remove a majority of the ammonium chloride salt and the conversion of the filtrate to an aqueous solution by the addition of water. If filtration is used to remove a majority of the salts, it is preferred to use a solvent in which the salts have a low solubility.

A third step involves the removal of solvent from an aqueous solution. The aqueous solution is prepared prior to solvent removal either directly, by the addition of water, or as the result of a prior step, such as the addition of water either (a) to a filtrate as noted above for the second step, or (b) to the reaction mixture prior to deionization. Solvent is removed from the aqueous solution by conventional techniques, such as vacuum distillation (evaporation) or phase extraction. If the solvent is removed by vacuum distillation, it is necessary to use a solvent which has a boiling point below that of water. If the solvent is removed by phase extraction, the solvent can have a boiling point higher than water. The solvent is removed while keeping the solution temperature below 25° C., which results in an aqueous solution containing 10–40% of hydrophilic monomer.

A fourth step involves the purification of the hydrophilic monomer by ion-exchange, i.e., a deionization step, from an aqueous solution. The aqueous solution is prepared prior to deionization either directly, by the addition of water to the reaction mixture to be deionized, or as the result of a prior step, such as either (a) addition of water to the filtrate following filtration or (b) addition of water to the reaction mixture prior to solvent removal. Any method can be used for removing all of the ionic moieties (primarily aminoalcohol, hydrochloride (HCl) and (meth)acrylic acid) from the aqueous solution can be used. In one embodiment, the deionization is performed by passing the aqueous solution through a mixed-bed ion-exchange column. Alternatively, deionization is performed in a batch process by adding a mixed-bed ion-exchange to the aqueous solution and then filtering the solution to remove the ion-exchanger. Deionization can also be performed using a cationic exchanger and an anionic exchanger in series.

The deionized, solvent-free, aqueous solution is the final product which can be used directly as described herein or can be concentrated further for storage. The hydrophilic monomer produced in accordance with this process has high purity. Specifically, the hydrophilic monomer solution does not contain any (1) esterification products, (2) oligomers or (3) salts. Thus, the hydrophilic monomer solution produced in accordance with this process can be used directly.

Several combinations of the above steps can be used in accordance with the present invention to produce the hydrophilic monomers. These combinations are outlined as follows:

Embodiment A: reaction⇒filtration⇒solvent removal⇒deionization;

Embodiment B: reaction⇒filtration⇒deionization⇒solvent removal;

Embodiment C: reaction⇒solvent removal⇒deionization; and

Embodiment D: reaction⇒deionization⇒solvent removal.

Water is added before deionization or solvent removal for two reasons. One is to prevent the self-polymerization of resultant hydrophilic monomer at a concentrated state, and the other is to facilitate purification by ion-exchange. When using solvent evaporation as the means to remove the solvent, it is currently preferred to use either embodiment B or D above for the preparation of hydrophilic monomers according to the present invention. When using phase extraction as the means to remove the solvent, any embodiment can be used. It is preferred to deionize the aqueous solution prior to solvent removal, to prevent a minor amount of self-polymerization which may occur if the solvent is removed prior to deionization. In accordance with the above description, the preparation of hydrophilic monomers in high purity and high yield, in a simple manner on a large scale in accordance with the preferred embodiments of the present invention, is performed by (i) conducting the reaction to avoid esterification, (ii) deionizing the resulting reaction mixture before solvent removal, and (iii) removing the organic solvent. The product has the following properties: (1) it is free of the hybrid crosslinker, the byproduct formed by reactions of both the amino and hydroxy groups on the aminoalcohols with (meth)acryloyl chloride, according to HPLC analysis; (2) it contains 10–40% hydrophilic monomer; (3) it has a pH of between 6 and 8 at 25° C.; (4) it has a conductivity of no more than 20 $\mu$S/cm at 25° C.; and (5) it has a viscosity of no more than 10 cPs at 25° C.

The hydrophilic monomers of the present invention, selected from the group consisting of N-(hydroxethyl)acrylamide or N-(hydroxyethyl)methacrylamide (hereinafter N-(hydroxy-ethyl)(meth)acrylamides) or N,N-di(hydroxyethyl)acrylamides or N,N-di(hydroxyethyl)methacrylamides (hereinafter N,N-di(hydroxyethyl)(meth)acrylamides)and mixtures thereof, preferably HEAA, can be used in electrophoresis applications well known in the prior art, including separation of macromolecules such as proteins and DNA, in gel electrophoresis or capillary electrophoresis, in sequencing DNA and coating capillary electrophoresis tubes. In these applications, the hydrophilic monomer is used in place of all or part of the acrylamide. Thus, the present invention also provides gels and electrophoresis compositions based on these specified monomers, preferably HEAA. In the discussion which follows, specific reference will be made to HEAA-based gels for illustration purposes only. It is to be understood that any of the specified hydrophilic monomers or mixtures thereof can be used for preparing the gels and electrophoresis compositions described herein.

The HEAA-based electrophoresis gels are prepared in a similar way to polyacrylamide gels, with the exception that HEAA monomer is substituted for all or part of the acrylamide monomer. Therefore, typical HEAA-based gels are formed in electrophoresis buffers by the free radical copolymerization of HEAA and optional comonomer with crosslinker, N,N'-methylene bisacrylamide (BIS) using ammonium persulfate (APS) and N,N,N',N'-tetramethylethylenediamine (TEMED) as initiator. In addition, the HEAA-based gels may also contain a denaturant, such as, but not limited to, urea or N-methylpyrrolidinone. The usable gel concentration (% T) is from 3% to 30%. Since HEAA has a higher formula weight (F.W.=115) than acrylamide (F.W.=71), the crosslinker level on a weight basis (% C) in HEAA-based gel needs to be reduced in order to keep the crosslinking density of the gel at about the same level. The Examples herein demonstrate the applications of HEAA-based gels for the electrophoretic separations of proteins, double-stranded DNA fragments, and automated DNA sequencing. These examples show that HEAA-based gels rival the resolution of polyacrylamide gels, and often have a longer shelf life than polyacrylamide gels.

Comonomers which can be used in combination with HEAA are water-soluble monomers including, but not limited to, acrylamide, methacrylamide, N,N-dimethylacrylamide (DMA), isopropylacrylamide, N-methylolacrylamide, N-vinylpyrolidone, N-vinylformamide, N-vinyl acetamide, other mono- and di-substituted hydroxyalkyl(meth)acrylamides of this invention, hydroxyethyl(meth)acrylate, polyethylene glycol mono(meth)acrylates, olefinic agarose and the like. The selection of comonomer is dependent on the specific electrophoretic application. For example, if protein separations are performed, it has been found that DMA is not useful as a comonomer. As with polyacrylamide gels, crosslinkers having polymerizable olefinic unsaturation may be used with the HEAA monomer in place of BIS to prepare electrophoresis gels. Crosslinkers are used in an amount of about 0.01 to about 2.0 wt %. Such suitable crosslinkers include, but are not limited to, piperazine diacrylamide (PDA), bisacrylamido-methyl-ether (BAME), N,N'-diallyl-tartardiamide (DATD), ethylene diacrylate, ethylene dimethacrylate, N,N'(1,2-dihydroxyethylene)bisacrylamide, N,N'N"-triallycitric triamide, poly(ethylene) glycol diacrylate, N,N'-bisacryloyl cystamine and olefinic agarose and the like.

In addition to APS/TEMED, other free radical polymerization initiators such as thermal/chemical initiators and photoinitiators can be used. Thermal/chemical initiators include, but are not limited to, benzoyl peroxide, t-butylhydroperoxide, hydrogen peroxide-$Fe^{2+}$-ascorbic acid, persulfate salts in conjunction with dimethylethylenediamine (DEMED), or B-dimethylaminopropionitrile, ammonium persulfate-metabisulfite, persulfate-TEMED-hydrosulfite, 2-(carbamoylazo)isobutyronitrile, 2,2'-azobis (N,N'-dimethyleneisobutyramidine)dihydrochloride, and 2,2'-azobis(2-amidino-propane)dihydrochloride.

Photoinitiators of aqueous soluble or dispersible compounds include, but are not limited to, riboflavin; mono- and di-carbonyl compounds, such as benzoylcyclohexanol, acetophenones (di- or tri-) substituted at the 2 position, 2,2 dimethoxy-2-phenylacetophenone, 2,2-diethoxyacetophenone, 2-hydroxy-2-methyl-1-propiophenone, 2 methoxy-2-phenylacetophenone, Michler's ketone [4,4'-bix (dimethylamino)-benzophenone], 4-carboxybenzophenone, benzophenone, diamino benzophenone, 9,10-phenanthrenequinone-3-sulfonate potassium salt, 1,2-naphtho-quinone-2-sulfonate potassium salt, 1,4-naphthoquinone-2-sulfonate potassium salt, 4-tri-chloromethyl-4-methyl-2,5-cyclohexadienone, benzoin ethers such as benzoin methyl ether and other benzoins, fluoroenones, and other aromatic water-soluble or dispersible mono- and di-carbonyl compounds; dyes such as methylene blue, new methylene blue, xanthine dyes, acridine dyes, thiazine dyes, phenazine dyes, camphorquinone dyes. Photoinitiators can be used with hydrogen donors including N,N-dimethylaminobenzoic acid, N,N'-dimethylaminoethanol, N-methyl diethanol amine, sodium p-toluene sulfate, and triethanolamine.

In addition to precast gels, preformulated compositions for use in electrophoresis are also provided by the present invention. The preformulated solutions comprise the ingredients listed above with respect to the HEAA-based gels in a suitable electrophoresis buffer, such as TBE, except the free radical initiator is not included. Gels are made from preformulated compositions by the addition of a free radical initiator.

Compositions for use in capillary electrophoresis include a coating composition and a sieving composition. The coating composition for capillary electrophoresis comprises an aqueous solution of HEAA, and the sieving composition comprises an aqueous solution of HEAA linear polymer. As with electrophoretic gels, the linear polymer may be an HEAA homopolymer or a copolymer of HEAA and one or more comonomers. Coating electrophoresis tubes for capillary electrophoresis is described in U.S. Pat. Nos. 4,680,201, 5,221,447 and 5,605,613. Separation and sequencing of DNA by capillary electrophoresis have been described by Dovichi (*Electrophoresis* 18:2393–2399 (1997)), Cheng et al. (*J Chromatography B*. 669:113–123 (1995)), Carrilho et al. (*Analytical Chemistry* 68:3305–3313 (1996)), and Madabhushi (*Electrophoresis* 9:224–230 (1998)).

Electrophoretic methods using the specified hydrophilic monomers alone or in combination with comonomers, preferably acrylamide, are performed using conventional techniques. It has been found that gels and linear polymers prepared in accordance with the present invention have as good of resolution as seen for acrylamide gels or linear polymers.

EXAMPLES

The present invention is described by reference to the following Examples, which are offered by way of illustration and are not intended to limit the invention in any manner. Standard techniques well known in the art or the techniques specifically described below were utilized. All raw materials were purchased from Aldrich Chemical Company, Milwaukee, Wis., and used as received, unless otherwise specified. Acryloyl chloride and methacryloyl chloride were used directly or were distilled before use. The mixed-bed ion-exchange resin Amberlite™ MB-150 was washed with appropriate solvent before use, as recommended by the manufacturer.

Example 1

Preparation of HEAA by Prior Art Method

In this example, HEAA was prepared according to the procedure reported by Chen (*ACS Symposium Series* 322:283–290 (1986)).

To a one liter, four-neck, round bottom flask equipped with a mechanical stirrer, a thermometer, a 400 mL dropping funnel, and nitrogen inlet/outlet, 122 g of ethanolamine (2 moles) and 250 mL of acetonitrile were added. The mixture was cooled down to −15° C. with an ice/water/salt bath. To this cold solution, 94.3 g of acryloyl chloride (1 mole) in 250 mL of acetonitrile was added through the dropping funnel. The addition rate was controlled so that the reaction temperature was kept about −15° C. After the reaction, the mixture was filtered to remove ethanolamine-HCl salt. To the filtrate, 300 mg of 4-methoxyphenol was added, and acetonitrile was removed by vacuum distillation. The solution temperature was kept below 25° C. to prevent free radical polymerization. The complete removal of acetonitrile resulted in either a viscous liquid or a solid mass. The viscous liquid is soluble in water, but the aqueous solution had a very high viscosity. The solid mass could not be dissolved in water. It is believed that polymerization by Michael addition reaction occurred during acetonitrile removal. The polymerization reaction is shown below:

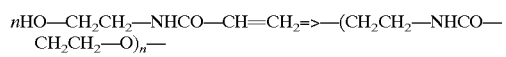

At a low level of polymerization, water soluble oligomers were formed. At a high level of polymerization, water insoluble polymers were formed. In either case, the final product could not be used to prepare electrophoresis gels.

Example 2

Preparation of HEAA by Prior Art Method

HEAA was prepared according to the procedure reported by Saito et al. (*Macromolecules* 29:313–319 (1996)). It was found that the crude product from the ethyl acetate phase (before silica chromatography) contained several components and the yield of HEAA was below 20%, as indicated by HPLC analysis. The yield will be even lower after silica gel chromatography purification. The crude product could not be polymerized by APS/TEMED.

Example 3

Preparation of HPAA or HEAA by Prior Art Method

In this example, HPAA was prepared according to the procedure of Righetti (WO 97/16462).

To a 500 mL, four-neck round bottom flask equipped with a mechanical stirrer, a thermometer, a 200 mL dropping funnel, and a nitrogen inlet/outlet, 18.8 g of acryloyl chloride (0.2 moles) was added. After cooling the acryloyl chloride to −40° C. in an acetone/dry ice bath, 150 mL of anhydrous ethanol pre-cooled to −40° C. was added. To this cold solution, 30.0 g of 3-amino-1-propanol (0.4 moles) in 150 mL of anhydrous ethanol was added through the dropping funnel. The addition rate was controlled so that the reaction temperature was kept at −40° C. After the addition, the reaction was continued at 5° C. for 5 hours. Ethanol was removed by evaporation, and the residue was dissolved in acetone. After filtering out the 3-amino-1-propanol HCl salts, the acetone solution was passed through a silica column, eluted with acetone. The eluate was collected and acetone was removed by evaporation. Water was added to the residue to yield an aqueous solution of 80 g. The aqueous solution contained 14% of HPAA, according to vacuum oven analysis. This monomer solution was used for gel electrophoresis in Example 10.

HEAA was also prepared in accordance with this procedure. The method required the complete removal of ethanol by vacuum distillation. It was found that the evaporation residual is very viscous, and so is the aqueous solution of the residue. Furthermore, a white precipitate was formed when the aqueous solution was mixed with acetone. This precipitation indicates that premature polymerization occurred during the evaporation step.

Example 4

Preparation of HEAA

Acetone was used as the solvent, triethylamine was used as the base to absorb the HCl generated, and water was added to the monomer before the removal of acetone to prevent polymerization of monomer.

To a one liter, four-neck round bottom flask equipped with a mechanical stirrer, a thermometer, a 400 mL dropping funnel, and a nitrogen inlet/outlet, 61 g of ethanolamine (1 mole), 101 g of triethylamine (1 mole), and 250 mL of acetone were added. The mixture was cooled down to −20° C. with an acetone/dry ice bath. To this cold solution, 94.3 g of acryloyl chloride (1 mole) in 250 mL of acetone was added through the dropping funnel. The addition rate was controlled so that the reaction temperature was kept about −20° C. After the reaction, the ethanolamine-HCl salts were filtered out. The filtrate was mixed with 300 mg of 4-methoxyphenol and 500 mL of deionized water. Acetone was removed by vacuum distillation. The remaining aqueous solution was passed through a mixed-bed ion-exchange column packed with 100 g of Amberlite™ MB-150. A total of 600 g of eluate was collected. The aqueous solution had a viscosity of only 2.0 cPs at 25° C., indicating that polymerization did not occur. However, HPLC analysis indicated that the obtained monomer was not pure. The HPLC chromatogram of reaction product is shown in FIG. 1 (top graph line). In addition to the major HEAA peak at 3.2 minutes, there was a minor peak at 11.2 minutes, which is attributed to the hybrid crosslinker, acrylamido-ethyl-acrylate.

Example 5

Preparation of HEAA

Acetonitrile was used as the solvent, ethanolamine was used as the base to absorb the HCl generated, and water was added to the monomer before the removal of acetonitrile to prevent polymerization of monomer.

To a one liter, four-neck round bottom flask equipped with a mechanical stirrer, a thermometer, a 400 mL dropping funnel, and a nitrogen inlet/outlet, 122 g of ethanolamine (2 moles), and 250 mL of acetonitrile were added. The mixture was cooled down to 0° C. with an ice/water bath. To this solution, 94.3 g of acryloyl chloride (1 mole) in 250 mL of acetonitrile was added through the dropping funnel. The addition rate was controlled so that the reaction temperature was kept about 50° C. At the end of addition, the pH of the reaction mixture was adjusted to 7 with either acryloyl chloride or ethanolamine. While keeping the reaction solution cold (below 5° C.), the ethanolamine-HCl salts were filtered out. The filtrate was mixed with 500 mL of deionized water before removing acetonitrile from the solution by vacuum distillation. The remaining aqueous solution was passed through a mixed-bed ion-exchange column packed with 100 g of Amberlite™ MB-150. A total of 600 g of eluate was collected. The solution had a viscosity of 1.8 cPs at 25° C., indicating that polymerization did not occur. HPLC analysis indicated that the product was free of any impurities. The HPLC chromatogram of the reaction product is shown in FIG. 1 (bottom graph line). There was only one peak at 3.2 minutes, and no peak was observed at 11.2 minutes. The eluate was concentrated to 400 grams, and further analyzed. Solids Content, 23% (wt/wt); pH=7.2 at 25° C.; Conductivity=14 $\mu$S/cm at 25° C.; Viscosity=2.0 cPs at 25° C. The yield of HEAA was about 80%. This monomer solution was used for gel electrophoresis in Examples 10–13.

Example 6

Preparation of HEAA

In comparison with Example 5, the deionization of this example is performed before the evaporation of acetonitrile and in a batch process instead of a column process.

To a one liter, four-neck round bottom flask equipped with a mechanical stirrer, a thermometer, a 400 mL dropping funnel, and a nitrogen inlet/outlet, 122 g of ethanolamine (2 moles), 200 mg of 4-methoxyphenol and 250 mL of acetonitrile were added. A slow nitrogen surge was used to minimize material loss during the reaction. The mixture was cooled below 0° C. with an ice/water bath. To this solution, 90.5 g of freshly distilled acryloyl chloride (1 mole) in 250 mL of acetonitrile was added through the dropping funnel. The addition rate was controlled so that the reaction temperature was kept below 5° C. The ethanolamine HCl salts precipitated during the reaction. At the end of addition, the pH of the reaction mixture was adjusted to 7 with either acryloyl chloride or ethanolamine. While keeping the reaction solution cold (below 5° C.), the ethanolamine HCl salts were filtered out. To the filtrate, 500 mL of deionized water and 100 g of Amberlite™ MB-150 were added. The resin was removed by filtration after agitating for one hour. The acetonitrile and part of the water were removed by vacuum rotary evaporation, maintaining solution temperature below 300° C. The miscibility of the solution was checked with acetone (1 ml of solution with 4 ml acetone), and the conductivity of the solution was measured when the residue weight reached 500 g. If the acetone mixture was clear and the conductivity was less than 10 $\mu$S/cm, the filtrate was concentrated to about 400 g by vacuum distillation. The filtrate can be concentrated to 300 g if desired. The final solution has the following properties: HEAA concentration: 23% (wt/wt); pH=7.2 at 25° C; Conductivity=3.5 $\mu$S/cm at 25° C.; Viscosity=2.4 cPs at 25° C. The yield of HEAA was about 80%.

DOWEX MR-3C resin can be used in place of the Amberlite™ MB-150. The resin mixture is agitated until the conductivity of the supernatant is less than 2 $\mu$S/cm. Additional ion-exchange resin is added if needed.

Example 7

Preparation of HEAA

In comparison with Example 5, the reaction of this example is conducted at 1 M concentration and lower temperature and the deionization of this example is performed before removal of acetonitrile.

To a one liter, four-neck round bottom flask equipped with a mechanical stirrer, a thermometer, a 600 mL dropping funnel, and a nitrogen inlet/outlet, 122 g of ethanolamine (2 moles), 400 mg of 4-methoxyphenol and 500 mL of acetonitrile were added. The mixture was cooled below −20° C. with a dry ice/acetone bath. To this solution, 90.5 g of freshly distilled acryloyl chloride (1 mole) in 500 mL of acetonitrile was added through the dropping funnel. The addition rate was controlled so that the reaction temperature was kept below −10° C. At the end of addition, the pH of the reaction mixture was adjusted to 7 with either acryloyl chloride or ethanolamine. While keeping the reaction solution cold (below −10° C.), the ethanolamine HCl salts were filtered out. To the filtrate, 500 mL of deionized water was added. The mixture was passed through an ion-exchange column packed with 100 g of AmberliteTM MB-150. The eluate was concentrated to about 400 g by vacuum distillation. The final solution has the following properties: HEAA concentration: 21% (wt/wt); pH=7.8 at 25° C.; Conductivity=5.6 μS/cm at 25° C.; Viscosity=2.8 cPs at 25° C. The yield of HEAA was about 73%.

Example 8

Preparation of N-(2-hydroxyethyl)methacrylamide (HEMAA)

To a 500 mL, four-neck round bottom flask equipped with a mechanical stirrer, a thermometer, a 200 mL dropping funnel, and a nitrogen inlet/outlet, 48.8 g of ethanolamine (0.8 moles), 80 mg of 4-methoxyphenol and 100 mL of acetonitrile were added. The mixture was cooled below 0° C. with an ice/water bath. To this solution, 41.8 g of freshly distilled methacryloyl chloride (0.4 mole) in 100 mL of acetonitrile was added through the dropping funnel. The addition rate was controlled so that the reaction temperature was kept below 0° C. At the end of addition, the pH of the reaction mixture was adjusted to 7 with either methacryloyl chloride or ethanolamine solution. While keeping the reaction solution cold (below 5° C.), the ethanol-amine HCl salts were filtered out. To the filtrate, 200 mL of deionized water and 40 g of Dowex MR-3C resin, which was pre-washed with two bed volumes of 1/1 ratio acetonitrile/water mixture for three times, were added. The resin was removed by filtration after agitating for one hour. The filtrate was concentrated to about 160 g by vacuum distillation. The final solution has the following properties: HPLC and FT-1R analysis indicates there is no ester formation; HEMAA concentration: 23.5% (wt/wt); pH=6.9 at 25° C; Conductivity=3.9 μS/cm at 25° C.; Viscosity=1.9 cPs at 25° C. The yield of HEMAA was about 73%.

Example 9

Preparation of N-(3-hydroxypropyl)acrylamide (HPAA)

To a 250 mL, four-neck round bottom flask equipped with a mechanical stirrer, a thermometer, a 100 mL dropping funnel, and a nitrogen inlet/outlet, 30.0 g of 1-amino-3-propanol (0.4 mole), and 100 mL of acetonitrile were added. The mixture was cooled below 0° C. with an ice/water bath. To this solution, 18.1 g of freshly distilled acryloyl chloride (0.2 mole) in 50 mL of acetonitrile was added through the dropping funnel. The addition rate was controlled so that the reaction temperature was kept below 0° C. After the addition was finished and the agitation was turned off, the reaction solution separated into two liquid phases. The bottom layer viscous salt solution phase was discarded. To the top layer acetonitrile solution phase, 100 mL of deionized water was added. After removing all acetonitrile by vacuum distillation, the aqueous solution was passed through a mixed bed ion-exchange column packed with 20 g of Dowex MR-3C resin. A total of 76 grams of eluate was collected. The final solution has the following properties: HPLC and FT-IR analysis indicates there is no ester formation; HPAA concentration: 7.2% (wt/wt); pH=5.6 at 25° C; Conductivity=56.6 μS/cm at 25° C.; Viscosity=1.1 cPs at 25° C. The relative low yield of HPAA is due to the fact that HPAA is soluble in the salt phase. HPAA in the salt phase can be recovered by acetone extraction since HPAA is soluble in acetone, and the salt is insoluble.

N-(2-hydroxypropyl)acrylamide, N-(2-hydroxypropyl)methacrylamide, N,N-di-(2-hydroxyethyl)acrylamide, N-(hydroxyethyl)-N-(3-hydroxypropyl)methacrylamide, N-(1-chloro-ethyl-2-hydroxyethyl)acrylamide and N-(hydroxyethoxyethyl)acrylamide are prepared in a manner similar to that of Examples 5–9 above, using the appropriate starting materials.

Example 10

Gels for Protein Analysis

The performance of HEAA-based gels was assessed by electrophoretic separation of a 5 kD to 225 kD range molecular weight standard, and protein extracts of bacteria *E. coli*. Visualization of the results was performed by staining the gels with Coomassie Brilliant Blue. The results of HEAA-based gels were compared with those of polyacrylamide gels, DMA-based gels and HPAA-based gels. All SDS-gel electrophoresis experiments were conducted under standard discontinuous buffer condition as described by Laemmli (*Nature* 277:680–685 (1970)), except that the buffer in the stacking gel was the same as that in the resolving gel (0.375M Tris-HCl, pH=8.8). The running buffer was Tris-Glycine (250 mM Tris., 250 mM Glycine, 0.1% SDS, pH=8.3). All four vinyl monomers were mixed with a crosslinker, BIS, to form gels. The crosslinker level (% C, obtained by dividing the amount of crosslinker by the sum of the crosslinker and monomer (and optional comonomer) multiplied by 100) was kept the same in the stacking (4% T; obtained by dividing the amount of the monomer, optional comonomer and crosslinker by the total volume of the solution multiplied by 100) and resolving (10% T) gels. APS/TEMED (0.1% in final gel solution) was used to initiate polymerization. All gels were cast in Novex plastic Mini-Cassettes (10 cm×10 cm×0.1 cm). The gels were allowed to polymerize at ambient temperature for one hour before use. The gels were run in a Novex Xcell II Mini-Cell at a constant voltage of 120 V until the tracking dye reached the bottom of the gel. The gel formulations and results are summarized in Table 1.

TABLE 1

Protein Gel Formulations and Separation Results

| Gel Formulation | Prior Art Gel #1 | Prior Art Gel #2 | Prior Art Gel #3 | Invention Gel #4 | Invention Gel D | Invention Gel E | Invention Gel F | Invention Gel G |
|---|---|---|---|---|---|---|---|---|
| Monomer | AA | HPAA (Ex. 3) | DMA | HEAA (Ex. 5) | HEAA (Ex. 5) | HBAA (Ex. 5) | HEAA (Ex. 5) | HEAA (Ex. 5) |
| Comonomer | | | | | AA | AA | AA | AA |
| Mon.:Comon. Ratio | | | | | 25:75 | 50:50 | 75:25 | 85:15 |
| Crosslinker (c) | BIS | BIS | BIS | BIS | BIS | BIS | BIS | BIS |
| % C (weight ratio of monomer to crosslinker) | 3.3 (29:1) | 1.8 (54:1) | 2.3 (42:1) | 2.5 (39:1) | 2.5 | 2.5 | 2.5 | 2.5 |
| Resolution | Good | Poor | Very poor | Good | Good | Good | Good | Good |
| Shelf Life (4° C.) | 3 Mo. | ND | ND | 12 Mo. | 3 MO. | 3 Mo. | >6 Mo. | >6 Mo. |

ND = Not Determined

The separation range was 25–225 kd. The quality of resolution of proteins in these gels were, in descending order: HEAA-based gels=polyacrylamide gels>HPAA-based gels>DMA-based gels. DMA-based gels have the worst resolution because DMA is the most hydrophobic. The poor resolution of HPAA-based gels in comparison with polyacrylamide gels is contrary to what was claimed by Righetti (WO 97/16462). The resolution of HEAA-based gels is comparable to that of polyacrylamide gels, indicating the hydrophilicity of HEAA is similar to that of acrylamide.

Figure 2A:
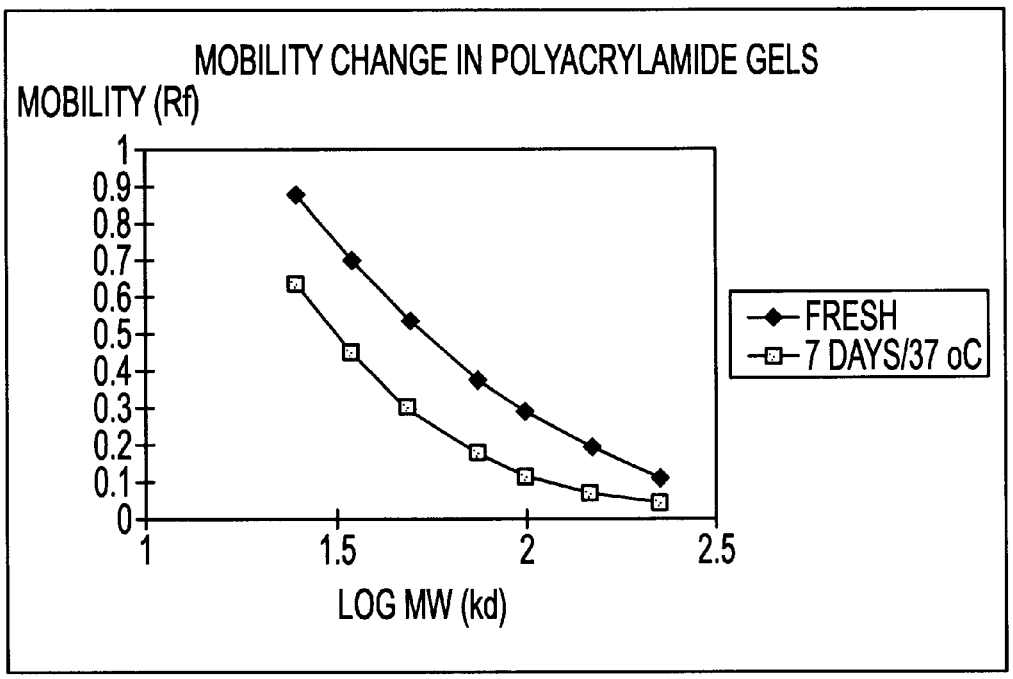
FIG. 2A uses a polyacrylamide gel and FIG. 2B uses HEAA-based gels. Mobility (Rf) was defined as the ratio of the distance migrated by protein molecule to the distance migrated by the tracking dye molecule.
Figure 2B:
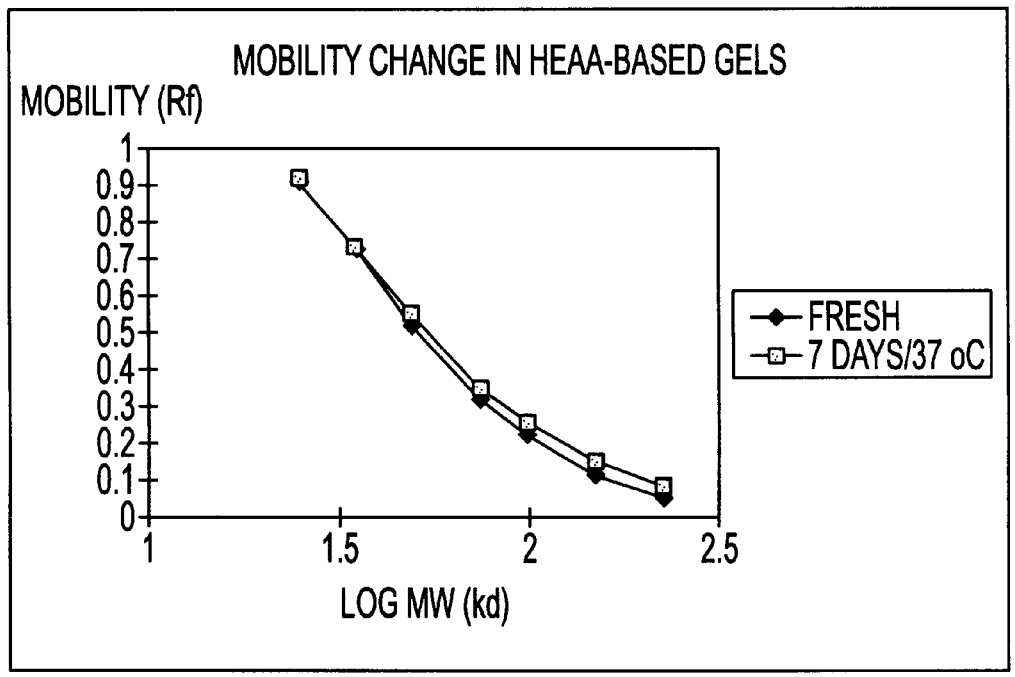
FIG. 2 shows the effect of gel aging on protein mobility during gel electrophoresis.

A large number of gels #1 and #4 were prepared and stored at 370° C. for different periods of time. The resolution of proteins in aged gels were compared with that in fresh gels. It was found that, in both cases, gel resolution deteriorated with aging, but polyacrylamide gels deteriorated at a much higher rate than HEAA-based gels. For example, polyacrylamide gels were completely useless for $E.\ coli$ protein separation after 7 days at 37° C., but HEAA-based gels still gave reasonable resolution after 20 days at 37° C. Based on the fact that standard polyacrylamide gels have a shelf life of 3 months at 4° C., it can be extrapolated that HEAA-based gels have a shelf life of at least 12 months at 4° C. The effect of aging on protein mobility in electrophoresis gels is shown in FIG. 2. For polyacrylamide gels (FIG. 2A), there is a substantial drop of protein molecule mobility after the gels are stored at 37° C. for 7 days. This drop is attributed to the hydrolysis of acrylamide moieties. The hydrolysis results in the incorporation of negatively charged carboxyl (—COO$^-$) groups onto the gel matrix, which in turn slows down the mobility of protein molecules by electroendosmosis. For HEAA-based gels (FIG. 2B), there is essentially no change in protein mobility after the gels are stored at 37° C. for 7 days, indicating that HEAA-based gels are more resistant to alkaline hydrolysis than polyacrylamide gels. For a discussion of gels D–G, see Example 14.

Example 11

Non-denaturing Gels for Double-Stranded DNA Fragments Separation

The performance of HEAA-based gels was assessed by electrophoretic separation of double-stranded (ds) DNA ladders (FMC Corporation, 20 bp, 100 bp and 500 bp). Visualization of the separation results was performed by staining the gels with ethidium bromide. The results were compared with standard polyacrylamide gels. 1 X TBE buffer (89 mM Tris, 89 mM boric acid, 2 mM EDTA, pH=8.3) was used as both gel buffer and running buffer. For both types of gels, BIS was used as a crosslinker, and APS/TEMED (0.1% in final gel solution) was used to initiate polymerization. All gels were cast in Novex plastic Mini-Cassettes (10 cm×10 cm×0.1 cm). The gels were set at ambient temperature for one hour before use. The gels were run in a Novex Xcell II Mini-Cell at a constant voltage of 120 V until the tracking dye reached the gel bottom. The gel formulations for ds DNA fragments separation and results are summarized in Table 2.

TABLE 2

Non-denaturing DNA Gel Formulations and Separation Results

| Gel Formulation | Prior art gel #5 | Invention gel #6 |
|---|---|---|
| Monomer | AA | HEAA (Ex. 5) |
| Crosslinker | BIS | BIS |
| % C (weight ratio of monomer to crosslinker) | 3.3 (29:1) | 2.0 (49:1) |
| % T | 10 | 10 |
| Sep. Range | 40–2000 bp | 40 bp–2000 bp |
| Resolution | Good | Good |

At the same crosslinking density level, i.e., the same monomer-to-crosslinker molar ratio, HEAA-based gels have comparable separation range and resolution as polyacrylamide gels. On the basis of the data of Example 10, it is expected that HEAA-based nondenaturing gels will have longer shelf life than nondenaturing polyacrylamide gels.

Example 12

Denaturing Gels for DNA Sequencing

Denaturing polyacrylamide gels are widely used for manual and automated DNA sequencing. DNA sequencing gels require very high resolution because single-stranded DNA fragments with only one nucleotide(nt) difference among several hundreds of nucleotides need to be separated. Denaturing HEAA-based gels for DNA sequencing are assessed on a commercially available automated DNA sequencer, OpenGene™ system, Visible Genetics Inc. Gels are prepared in 50 μm-thick MicroCel™ glass cassettes from VGI by photoinitiation using a conventional photoinitiator, such as 2,2-dimethoxy-2-phenyl-acetophenone and a UV source ranging form 200 to 500 nm. Denaturants, such as urea and N-methyl-pyrrolidinone (NMP), are added into the gels to prevent the formation of any secondary structure in single-stranded DNA fragments during electrophoresis. 1X TBE buffer (Tris 89 mM, boric acid 89 mM, EDTA 2 mM, pH 8.3) is used as gel buffer as well as running buffer. M13 mp18 DNA is used as template for PCR and sequencing reactions. The DNA sequence of M13 mp18 is available (GeneBank Accession #X02513). Nucleotides number 23 through 523 are used to assess the quality of DNA sequence data. The numbering of nts starts at the first A (adenine) in the HindIII restriction recognition site, and increases counter-clockwise towards the AvaII restriction site of this DNA. Read length at 99% accuracy is scored. This is defined as the length of consecutive nts that are read with ≦1% error. The primer for DNA sequencing is labeled with fluorescent dye CY5.5. The gels are run for 45 minutes at 1500 Volts and 51° C. Again, HEAA-based denaturing gels are compared with polyacrylamide denaturing gels, in terms of read length at 99% accuracy, and potential stability. The gel formulations are summarized in Table 3.

TABLE 3

DNA Sequencing Gel Formulations

| Gel Formulation | Prior art Gel #7 | Prior art Gel #8 | Invention Gel #9 | Invention Gel #10 |
|---|---|---|---|---|
| Monomer | AA | AA | HEAA (Ex. 5) | HEAA (Ex. 5) |
| Crosslinker | BIS | BIS | BIS | BIS |
| % C (weight ratio of monomer to crosslinker) | 3.3 (29:1) | 3.3 (29:1) | 1.5 (66:1) | 1.5 (66:1) |
| % T | 6 | 7 | 6 | 7 |
| Denaturant | 7 M urea | 25% NMP | 7 M urea | 25% NMP |

It is expected that Prior art Gel #7 has a read length of 300–350 nts with 99% accuracy, because it is widely used for DNA sequencing. Since neither acrylamide nor urea is stable in TBE buffer, the shelf life of a premix solution or a precast gel made from this combination is expected to be short. In Prior art Gel #8, a stable organic denaturant, N-methyl-pyrrolidinone (NMP), is used in combination with acrylamide. It is expected that the resolution is poor and the read length is below 100 nt at 99% accuracy. This result suggests that NMP interfered with the formation of the polyacrylamide gel. It is found that both invention Gels #9 and #10 have a read length of 300–350 nts with 99% accuracy, comparable with Prior art Gel #7. Since urea is used as the denaturant in Gel #9, a premix solution or a precast gel made from this combination is not expected to have a long shelf life. However, both HEAA monomer and the NMP denaturant are stable in Gel #10, so the premix solution and precast gel are expected to have longer shelf life than Prior art Gel #7.

Example 13

Denaturing Gels for DNA Sequencing

Denaturing HEAA-based gels for DNA sequencing were tested on a commercial automated DNA sequencer, Prism™ 377 DNA sequencer (PE-Applied BioSystems, Foster City, Calif.). Gels were prepared in 0.2 mm-thick 36 cm-long glass cassettes using APS/TEMED as the polymerization initiator system, and in the absence or presence of comonomer, acrylamide. Urea was added to 36 wt % (6M) and 1X TBE was used as gel buffer as well as running buffer. M13mp18 DNA (GeneBank Accession #X02513) nucleotides 4 through 800 were used to assess the quality of resolution (nts were numbered according to Example 12). The sequencing primer was labeled with PE-Applied Biosystems' Big Dye chemistry. The gels were run for 3.5 hours at the "4X" running condition (2400 scans/hr). Read length at 98.5% was scored, defined as the length of consecutive nts that were read with ≦1.5% error.

TABLE 4

DNA Sequencing Gel Formulations

| Gel Formulation | #11 (Prior Art) | #12 (Invention) | #13 (Invention) |
|---|---|---|---|
| Monomer | Acrylamide | HEAA | Acrylamide/HEAA = 80/20 Weight ratio |
| Crosslinker | BIS | BIS | BIS |
| % T | 4.5% | 6% | 5.5% |
| % C | 3.3% | 1.25% | 1.25% |
| Buffer | 1 X TBE | 1 X TBE | 1 X TBE |
| Denaturant | 6 M urea | 6 M urea | 6 M urea |
| APS | 0.05% | 0.05% | 0.05% |
| TEMED | 0.07% | 0.07% | 0.07% |
| Read length at 98.5% accuracy | 510–665 nt | 550–730 nt | 600–650 nt |

The results indicate that HEAA based gels are at least as good as acrylamide gels for automated DNA sequencing. The pre-formulated gel solution of HEAA should be more stable than a gel solution of acrylamide.

Example 14

HEAA and Acrylamide Copolymer Gels for Protein Analysis

Gels for protein analysis were prepared in accordance with Example 10 using the monomers shown in Table 5. BIS was used as crosslinker, keeping the crosslinking level (% C) constant at 2.5, and the total weight of the monomer and crosslinker at 10% T. The ratio of the different monomers (HEAA and acrylamide) were as shown in Table 5. Protein samples were analyzed on mini-gels using the method described in Example 10. The gel formulation and separation results are shown in Table 5.

TABLE 5

Protein Gel Formulations and Separation Results

|  | HEAA (monomer %) | Acrylamide (monomer %) | Resolution (time zero) | Resolution (7 days at 37° C.) |
|---|---|---|---|---|
| Gel A (prior art) |  | 100% | Good | Bad |
| Gel C (invention) (=#4) | 100% |  | Good | Good |
| Gel D (invention) | 25% | 75% | Good | Bad |
| Gel E (invention) | 50% | 50% | Good | Bad |
| Gel F (invention) | 75% | 25% | Good | Good |
| Gel G (invention) | 85% | 15% | Good | Good |

It has been found that gels which contain 1–100% HEAA and 0–99% comonomer, such as acrylamide and others disclosed herein, all have good resolution when freshly made. It has further been found that the percentage of HEAA in the total copolymer affects the storage stability of the precast gel when the comonomer is less stable than HEAA.

Example 15

Preparation of Linear HEAA Polymers

To a 50 mL round-bottom flask, 12.1 mL of 33% (w/v) HEAA solution (4 g of HEAA), 0.8 ml of isopropanol, an 7.1 mL of deionized water were added. The solution was mixed and degassed for 20 mins under 40 mmHg vacuum. After warming the solution to 40° C., 100 μl of 10% APS solution and 20 μl of TEMED were added and mixed by shaking. The polymerization was conducted at 40° C. for 1 hour and the resulting polymer solution was lyophilized overnight. The white solids were extracted with acetone in a Soxhlet apparatus for two hours, and then dried in a vacuum oven for two hours. A total of 3.9 grams of polymer was obtained (97.5% yield). The polymer is soluble in water at ambient temperature, and a 10% aqueous solution has a viscosity of 1030 cPs, when measured with a Brookfield viscometer (#4 spindle, 60 rpm).

Example 16

DNA Sequencing by Capillary Electrophoresis

The use of HEAA for sequencing DNA by capillary electrophoresis is tested by following the procedure of Ruiz-Martinez et al. (*Anal. Chem.* 68:3305–3315 (1996)) in which a linear polymer of HEAA is used in place of the linear polyacrylamide of Ruiz-Martinez et al. Using low viscosity linear HEAA homopolymers at 6% concentration, elevated column temperature (50° C.) and moderately high field (150 V/cm), rapid sequencing analysis using M13mp18 template is obtained with excellent accuracy.

Example 17

Short Tandem Repeat Sizing

The sizing capability of slab gel electrophoresis and of capillary electrophoresis (CE) for short tandem repeat (STR) fragments is compared using the technique described by Deforce et al. (*J. Chromatography* 8:149–155 (1998)). Both systems used automated laser fluorescence detection to detect four fluorescent dyes, enabling the use of an internal lane standard within each sample. The STR fragments are amplified using a multiplex polymerase chain reaction in which the STR fragments Hum CD-4, Hum TH01, Hum D21S11 and Hum SE33 are amplified simultaneously. The reproducibility of the size calling is determined for both systems. The CE system produced results comparable to those obtained on the slab gel system.

INDUSTRIAL UTILITY

Hydrophilic monomers are prepared simply and on a large scale in accordance with the present invention. The hydrophilic monomers, particularly HEAA, are useful for preparing electrophoretic compositions and gels and are further useful for coating capillary tubes. The electrophoretic compositions and gels can be used for any electrophoretic method to separate macromolecules or sequence DNA or the like. In addition, the hydrophilic monomers can be used in any application in which related (meth)acrylate monomers, especially hydrophilic (meth)acrylate monomers, are used. Such applications include gel beads for chromatography separation, coatings for contact lenses, monomers for preparing contact lenses, water soluble polymeric compositions and the like.

The present invention may be embodied in other specific forms without departing from the spirit or essential attributes thereof and, accordingly, reference is made to the appended claims, rather than the foregoing specification, as indicating the scope of the invention.

What is claimed is:

1. A composition for preparing an electrophoretic gel which comprises 3–30 wt % of a monomer composition and about 0.01 to about 2.0 wt % of a crosslinker in an electrophoresis-compatible buffer, said monomer composition comprising 75 wt % or more of a hydrophilic monomer and 25 wt % or less of a comonomer, said hydrophilic monomer selected from the group consisting of N-(hydroxyethyl)(meth)acrylamide, N,N-di(hydroxyalkyl)(meth)acrylamide and mixtures thereof.

2. The composition of claim 1, which further comprises a denaturant.

3. The composition of claim 1, wherein said hydrophilic monomer comprises N-(2-hydroxyethyl)acrylamide.

4. The composition of claim 1, wherein said monomer composition comprises 75 wt % N-(2-hydroxyethyl)acrylamide and 25 wt % acrylamide.

5. The composition of claim 1, wherein said monomer composition comprises 100 wt % N-(2-hydroxyethyl)acrylamide.

6. The composition of claim 1, which further comprises N,N'-methylene bisacrylamide as a crosslinker.

7. A composition useful as a sieving medium for capillary electrophoresis which comprises 0.1–30 wt % of a linear polymer formed from a monomer composition comprising 1–100 wt % of a hydrophilic monomer and 0–99 wt % of a comonomer in an electrophoresis-compatible buffer, said hydrophilic monomer selected from the group consisting of N-(hydroxyethyl)(meth)acrylamide, N,N-di(hydroxyalkyl)(meth)acryl-amide and mixtures thereof.

8. The composition of claim 7, wherein said monomer composition comprises 10–100 wt % of said hydrophilic monomer and 0–90 wt % of a comonomer.

9. The composition of claim 7, wherein said monomer composition comprises 20–100 wt % said hydrophilic monomer and 0–80 wt % of a comonomer.

10. The composition of claim 7, wherein said monomer composition comprises 30–100 said hydrophilic monomer and 0–70 wt % of a comonomer.

11. The composition of claim 7, wherein said hydrophilic monomer comprises N-(2-hydroxyethyl)acrylamide.

12. The composition of claim 7, wherein said monomer composition comprises 75 wt % N-(2-hydroxyethyl)acrylamide and 25 wt % acrylamide.

13. The composition of claim 7, wherein said monomer composition comprises 100 wt % N-(2-hydroxyethyl)acrylamide.

14. A method of separating molecules in an electric field which comprises contacting a mixture of molecules with a separation medium while being subjected to an electric field sufficient to cause separation of said molecules in said separation medium, which said separation medium comprises either (a) a gel comprising the produce formed by crosslinking polymerization of a monomer composition comprising 75 wt % or more of a hydrophilic monomer and 25 wt % or less of a comonomer, or (b) a sieving medium comprising a linear polymer formed from a monomer composition comprising 1–100 wt % of a hydrophilic monomer and 25 wt % of less 0–99 wt % of a comonomer, said hydrophilic monomer selected from the group consisting of N-(hydroxyethyl)(meth)acrylamide, N,N-di(hydroxyal)(meth)acrylamide and mixtures thereof.

15. The method of claim 14, wherein said hydrophilic monomer comprises N-(2-hydroxyethyl)acrylamide.

16. The method of claim 14, wherein said monomer composition comprises 75 wt % N-(2-hydroxyethyl)acrylamide and 25 wt % acrylamide.

17. The method of claim 14, wherein said monomer composition comprises 100 wt % N-(2-hydroxyethyl)acrylamide.

* * * * *